(12) United States Patent
Sciuto et al.

(10) Patent No.: US 10,364,299 B2
(45) Date of Patent: Jul. 30, 2019

(54) DERIVATIVES OBTAINED FROM HYALURONIC ACID AND CARNOSINE

(71) Applicants: Sebastiano Sciuto, Pedara (IT); CONSIGLIO NAZIONALE DELLE RICERCHE, Rome (IT); FIDIA FARMACEUTICI S.P.A., Abano Terme (IT)

(72) Inventors: Sebastiano Sciuto, Pedara (IT); Valentina Greco, Priolo Gargallo (IT); Enrico Rizzarelli, Catania (IT); Francesco Bellia, Belpasso (IT); Valeria Lanza, Catania (IT); Susanna Vaccaro, Syracuse (IT); Luciano Messina, Syracuse (IT)

(73) Assignees: Sebastiano Sciuto, Padara (IT); CONSIGLIO NAZIONALE DELLE RICERCHE, Rome (IT); FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 15/500,640

(22) PCT Filed: Jul. 30, 2015

(86) PCT No.: PCT/IB2015/055782
§ 371 (c)(1),
(2) Date: Jan. 31, 2017

(87) PCT Pub. No.: WO2016/016847
PCT Pub. Date: Feb. 4, 2016

(65) Prior Publication Data
US 2017/0246306 A1    Aug. 31, 2017

(30) Foreign Application Priority Data
Jul. 31, 2014 (IT) .............................. MI2014A1395

(51) Int. Cl.
*A61K 47/61* (2017.01)
*C08B 37/08* (2006.01)
*C07D 233/64* (2006.01)

(52) U.S. Cl.
CPC .......... *C08B 37/0072* (2013.01); *A61K 47/61* (2017.08); *C07D 233/64* (2013.01)

(58) Field of Classification Search
None
See application file for complete search history.

(56) References Cited

FOREIGN PATENT DOCUMENTS

| EP | 1 176 154 | * | 1/2002 |
|----|-----------|---|--------|
| EP | 1 176 154 A1 |  | 1/2002 |
| EP | 1 860 116 | * | 11/2007 |
| EP | 1 860 116 A1 |  | 11/2007 |
| WO | WO 2012/076961 A2 |  | 1/2002 |
| WO | WO 2012076961 | * | 6/2012 |

OTHER PUBLICATIONS

Mero et al. Hyaluronic Acid Bioconjugates for the Delivery of Bioactive Molecules. Polymers 2014, 6, 346-369; doi:10.3390/polym6020346.*
International Search Report (PCT/ISA/210) issued in PCT/IB2015/055782, dated Nov. 26, 2015.
Written Opinion (PCT/ISA/237) issued in PCT/IB2015/055782, dated Nov. 26, 2015.

* cited by examiner

*Primary Examiner* — Maury A Audet
(74) *Attorney, Agent, or Firm* — Birch, Stewart, Kolasch & Birch, LLP

(57) ABSTRACT

The present invention relates to a derivative of carnosine (β-alanyl-L-histidine) having formula (1), obtained by the functionalization of hyaluronic acid with carnosine.

17 Claims, 4 Drawing Sheets

Figure 1:
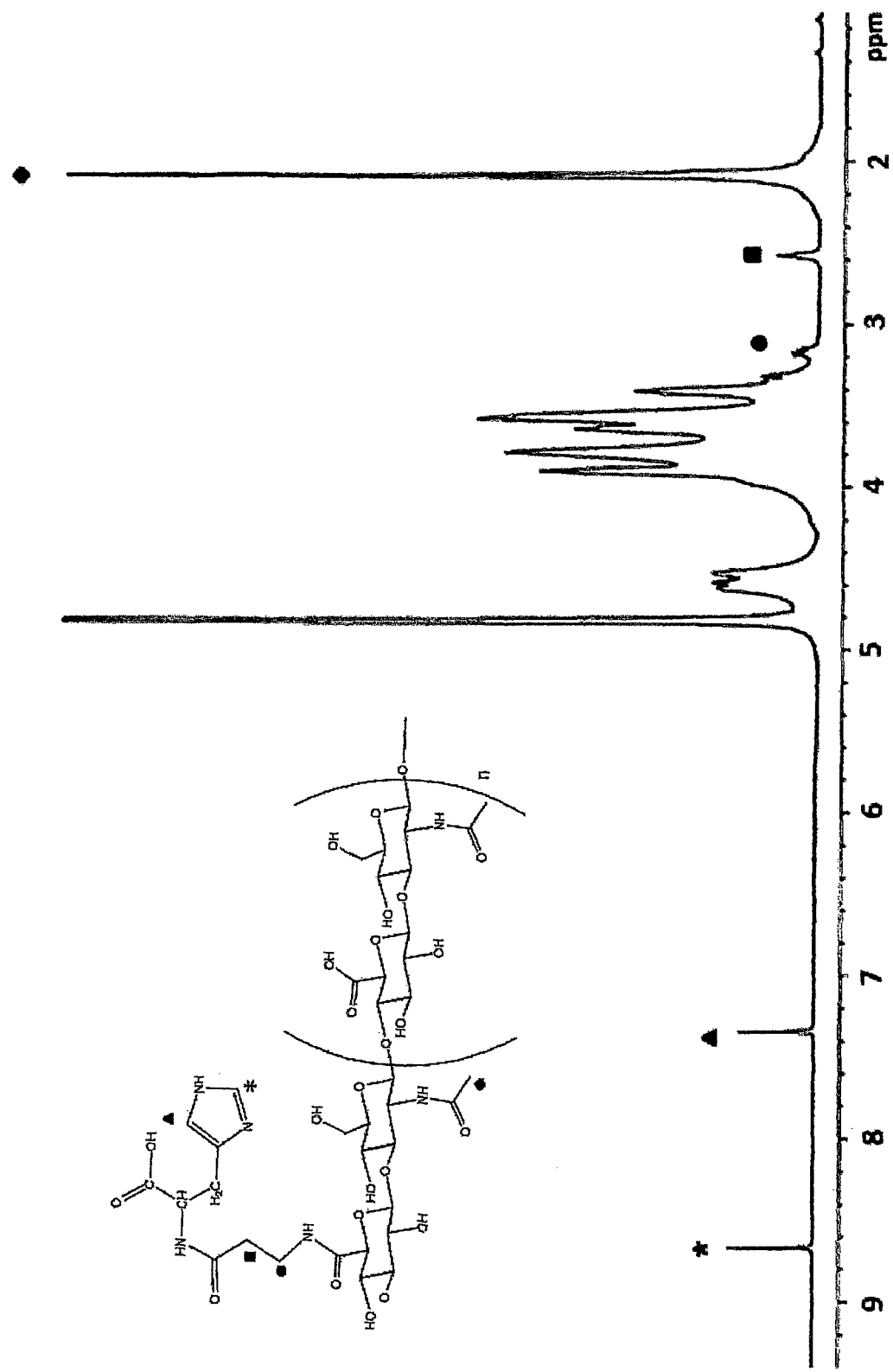

Stability of HyCar over time (•); Carnosine (■), Carnosine + HA (▲) and HA alone (♦).

DERIVATIVES OBTAINED FROM HYALURONIC ACID AND CARNOSINE

The invention relates to a derivative of carnosine (β-alanyl-L-histidine) having formula (1), obtained by the functionalization of hyaluronic acid with carnosine.

More specifically, the present invention relates to a compound having formula (1)

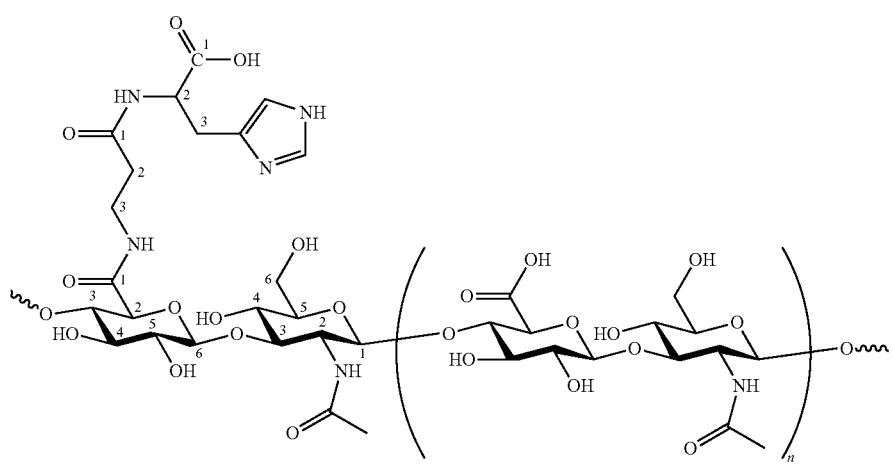

(1)

i.e. conjugated 3-N-hyaluronyl of 2-(3-aminopropanamide)-3-(1H-imidazol-4-yl)propanoic acid, or hyaluronyl-carnosine or 3-(1H-imidazol-4-yl)-2-(3-hyaluronamidopropanamide)propanoic acid.

The compound having formula (1) indicated above is the conjugate between carnosine dipeptide having formula (2)

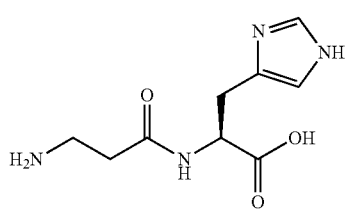

(2)

and hyaluronic acid, wherein the conjugation is obtained by the formation of an amide bond between the $NH_2$ group of carnosine, preferably protected at the carboxyl group, with one or more carboxyl groups of hyaluronic acid, preferably of an active derivative of hyaluronic acid, even more preferably of a COX ester having formula (3)

The invention also relates to a process for the preparation of conjugated 3-N-hyaluronyl of 2-(3-aminopropanamide)-3-(1H-imidazol-4-yl)propanoic acid (HyCar) and the formulations containing the same for pharmaceutical, cosmetic and nutraceutical use with an antioxidant, cicatrizing, chelating, gastroprotective (as a complex with $Zn^{2+}$) glucomodulatory, immunomodulatory, antitumoral, antigenotoxic, neuroprotective, anti-glycation, antifibrillogenic activity, anti-aging activity of the central nervous system, protective activity for damage due to ischemia/reperfusion, nephroprotective, hepato-protective activity.

The cellular respiration process generates an important and potentially dangerous by-product: the superoxide radical $O_2^{\cdot-}$, which can react, damaging them, with biological macromolecules such as proteins, DNA and lipids, and can generate other highly reactive species (ROS) such as $^{108}OH$, $RO_2^{\cdot}$, ROOH, $RO^{\cdot}$, $H_2O_2$ and $ONOO^{\cdot}$, which are potentially aggressive with respect to the cell system. All aerobic organisms have defense mechanisms against the $O_2^{\cdot-}$ radical, among which the main ones are dismutase superoxide (SOD) enzymes which catalyze the dismutation of $O_2^{\cdot-}$ into $O_2$ and $H_2O_2$. The hydrogen peroxide thus produced is, in turn, transformed into $H_2O$ by the catalase and by the glutathione peroxidase, thus preventing the formation of the $^{108}OH$ radical which would be generated by the Fenton reaction $(Fe(II)+)+H_2O_2 \rightarrow Fe(III)+^{108}OH+^-OH)$. Under certain pathological conditions (inflammatory processes, reperfusion injury, heart attacks, Alzheimer disease, ALS, etc.), the SOD enzymes can be insufficient for eliminating the excess of $O_2^{\cdot-}$ produced, and the biological tissues, in these cases, can undergo further damage. In some vertebrate

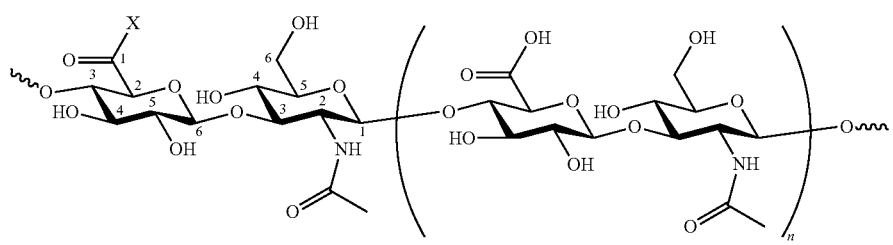

(3)

tissues, such as muscles or brain, characterized by a higher level of oxidative metabolism, a high level has been found of small molecules with an antioxidant activity such as glutathione and other peptides (carnosine, homocarnosine, anserine, etc.) which have the function of strengthening protection against oxidative stress processes. The protective activity of these peptides with respect to ROS has been widely discussed and demonstrated in literature ((Biochim. Biophys. Acta 1570, 89, 2002; Mol. Cells 13, 498, 2002; Biochem. J. 967, 241, 1988).

For carnosine, in particular, with respect to its anti-radical and anti-peroxidative properties, pre-clinical studies have demonstrated its capacity of preventing, and in some cases healing, cataract (Biochem. Int. 15, 1105, 1987; Biochim. Biophys. Acta 1004, 363, 1989). The anti-inflammatory activity has been demonstrated in tissues of the digestive system, in the eyes and skin ((U54508728 A, DE4316293, WO 01/52808 A). In addition, carnosine has shown inhibitory effects with respect to the oxidation of human LDL induced by Cu(II) (Eur. J. Med. Chem. 43, 373, 2008), and its scavenger activity with respect to the hydroxyl radical has been specifically demonstrated (Helv. Chim. Acta 85, 1633, 2002). With respect to the mechanism which allows carnosine to counteract the pathological effects of nitrosative stress, it has been demonstrated that direct interaction with nitric oxide is one of the possible paths (J. Neurosci. Res. 85, 2239, 2007), whereas only natural dipeptide drastically reduces the quantity of nitric oxide released by a No-donor. More recently, the efficacy of carnosine in reducing the activation of PARP-1, and also PARP-2, after induction of oxidative stress, has been demonstrated (Neurochem. Res. 35, 2144, 2010; Mol. Aspects Med. 32, 258, 2011). L-carnosine, on the other hand, analogously to N-monomethyl-arginine (known inhibitor of iNOS) down-regulates the expression of PRAP-1 (Neurochem. Res. 38, 50, 2013).

It is also interesting to observe that complexes of carnosine with Cu(II) show a synergic activity against two toxic species of radicals, $O_2^{\cdot-}$ and $HO^{108}$ $(DaltonTrans.$ 4406, 2003). Parallelly, it has also been observed that the presence of carnosine, anserine, homocarnosine and other similar peptides, improves the intestinal absorption of zinc, in practice, improving the bio-availability. This fact is particularly interesting in the zinc deficiency syndrome and in inflammatory intestinal diseases (Biomed. Res. Trace Elem. 12, 159, 2001).

The peptide nature of carnosine imposes various restrictions in its use, associated with its degradability on the part of specific peptidases. The use of N-acetyl-carnosine (WO 95/10294 A), which is degraded much more slowly than free carnosine (Clin. Chim. Acta 254, 1-21, 1996) has been proposed for overcoming this limitation. For the same purpose, the derivatization of carnosine with cyclodextrins, namely with compounds widely used as drug carriers, through the formation of a secondary amine (EP 1176154 A), has also been used. In this case, the cyclodextrin stabilizes the dipeptide, protecting it from the hydrolytic activity of carnosinase, as demonstrated for similar systems (J. Am. Chem. Soc. 120, 7030, 1998), consequently allowing carnosine to exert its biological activity, favoured by the presence of the oligosaccharide which eliminates the .OH radicals (Helv. Chim. Acta 85, 1633, 2002). Based on the same theory, a conjugated compound of carnosine with trehalose (EP 1860116 A1), was subsequently patented, as a system with antioxidant, antiglycation and antiplatelet activities. Also in this case carnosine is conjugated by means of bonds with the functional groups —OH of trehalose, forming secondary amines. The thus formed bond, certainly more stable than that obtainable by means of an ionic bond, not only protects carnosine at least partially from the enzymatic degradation, but it takes advantage of the known ability of trehalose to protect the proteins from conformational changes due to denaturing agents.

The compound having formula (1), object of the present invention, is obtained, on the contrary, by the covalent conjugation of carnosine with hyaluronic acid, through the formation of an amide bond between the carboxyl group of HA and an amine group of carnosine. Hyaluronic acid is a polymer consisting of repetitive disaccharide units, composed of glucuronic acid (β-D-glucopyranuronic acid) and acetyl glucosamine (2-acetylamino-2-deoxy-β-D-lucopyranosium), bound to each other by means of a glycoside bond between the anomeric carbon atom of the first and the C-3 of acetyl glucosamine. The disaccharide units are, in turn, bound to each other by means of glycoside bonds between the anomeric carbon of acetyl glucosamine of a disaccharide unit and the C-3 of the residue of glucuronic acid belonging to the following disaccharide unit, forming linear chains of variable length. The average molecular weight (MW) of HA depends on this length, said MW being extremely variable, depending also on the sources from which HA is obtained. In particular, the HA employed in the present invention can be obtained by extraction (for example from rooster combs), by fermentation, or by biosynthesis, having an average MW of between 90 and 230 kDa, preferably between 180 and 210 kDa. A further range of average MW useful for the purposes of the present invention is comprised between 500 and 730 kDa. In the present description average MW means "weight average MW", calculated according to the method of "intrinsic viscosity" (Terbojevich et al., *Carbohydr Res*, 1986, 363-377). Hyaluronic acid (HA) is a natural biodegradable polymer with a variety of applications in medicine, including molecular scaffolds for tissue engineering and viscosupplementation for the treatment of osteoarthrosis. Hyaluronic acid is currently used in the cosmetic field because of its protective and moisturizing properties. It represents one of the main constituents of the extra-cellular matrix (ECM) of the vertebrate tissues, and it can be found in almost all of the fluids and tissues of the body, such as the synovial fluid, vitreous humour and hyaline cartilage (Biomedical applications of hyaluronic acid. ACS Publications, p. 155-74, 2006; Biomaterials 25, 1339, 2004; Calcified Tissue Int. 7, 175, 1971; Dumitriu S., Polymeric biomaterials. New York: Marcel Dekker, 2002. ISBN:0-8247-8969-5). This biopolymer acts as a molecular scaffold and is linked to other molecules of the matrix, among which aggrecan (Garg H. G., Hales C. A., Chemistry and biology of hyaluronan. Oxford: Elsevier Science, 2004. ISBN:978-0-08-044382-9).

HA also has a role in various biological functions such as the regulation of cell adhesion and motility, manipulation of cell differentiation and proliferation and it provides the tissues with mechanic properties (Biomaterials 25, 1339, 2004). It has been demonstrated that some cell surface receptors (such as CD44, RHAMM and ICAM-1), interact with HA influencing some cell processes among which morphogenesis, cicatrization, inflammation and metastasis (Biomaterials 26, 359-71, 2005; Nat. Rev. Cancer 4, 528, 2004; J. Surg. Res. 147, 247, 2008; J. Cell. Sci. 103, 293, 1992). HA is also responsible for the viscoelasticity of some biological fluids (synovial fluid, vitreous humour of the eye) and it controls tissue hydration and the water transportation (Vet. Med. 53, 397, 2008). In addition, HA has been found, during embryonic development, in the umbilical cord, suggesting that HA composite materials can induce favourable conditions for the regeneration and growth of tissues (Acta Biomater. 6, 2407, 2010; Biomaterials 28, 1830, 2007; J. Control. Release 69, 1 69, 2000; Chem. Rev. 101, 1869, 2001; Biomaterials 24, 4337, 2003).

The characteristics of HA, including its consistency, biocompatibility and hydrophilicity have made it an excellent moisturizer used in cosmetic dermatology and in skin-care products (Vet. Med. 53, 397, 2008).

In patent application WO 2012/076961 A2, a compound comprising salified, or at least partially salified, hyaluronic acid with carnosine, is claimed; the objective of the inventor of this patent application is to obtain preparations that offer the biopharmacological properties of both compounds. In this case, however, due to the ionic nature of the bond which holds the two active principles together, when the compound claimed reaches the biological fluids, it will immediately release free carnosine which will be rapidly destroyed by the serum carnosinase. The conjugate having formula (1), object of the present invention, on the contrary and as previously considered, is characterized by the presence, between carnosine and hyaluronic acid, of a covalent bond of the amide type which is not immediately hydrolyzable; carnosine, in its conjugated form, is therefore more resistant to the action of serum carnosinase and the compound having formula (1) maintains the carnosine linked and intact for a period of time which is sufficient for allowing the same carnosine to reach the site where it will exert its action, giving a technical effect of slow release.

In a very surprising way, the Applicant has found and demonstrated that this bond not only, as expected, slows down the release of carnosine, being less hydrolyzable than the bonds previously described, but it mainly gives to the compound of formula (1) an antioxidant activity which is extremely high. The conjugation of HA and carnosine through an amide bond as herein claimed, increases the biological effect of carnosine to an extent definitely higher than the effect due to a simple protection from the enzymatic hydrolysis, and this was completely unexpected given that HA as such does not have antioxidant activity.

In the light of the above, the presence of hyaluronic acid in the conjugate object of the present invention synergistically enhances the action against the oxidative processes already present in carnosine, guaranteeing in the latter, a considerable stability with respect to serum carnosinase and consequently conferring a higher activity with respect to carnosine as such or as acetyl-derivative.

The percentage of carboxylic groups of hyaluronic acid conjugated through the amide bond with carnosine, ranges from 2 to 25%, preferably from 5 to 20%, and even more preferably is equal to 7% of the total carboxylic groups of HA.

An object of the present patent application also relates to the Cu (II) complex of the conjugate having formula (1).

The SOD-like antioxidant activity of the Cu (II) complex of the conjugate having formula (1) was in fact evaluated, verifying it in vitro by comparison with the Cu (II) complex of free carnosine and with the Cu (II) complex of non-conjugated hyaluronic acid. The results showed that the activity of the Cu (II) complex having formula (1) is extraordinarily higher with respect to the activity of the corresponding complexes of carnosine or hyaluronic acid.

An object of the present invention also relates to a process for the preparation of the compound having formula (1), wherein a derivative of hyaluronic acid is covalently conjugated with carnosine protected at the carboxyl group. The compound having formula (1) according to the present invention, was in fact synthesized starting from hyaluronic acid suitably activated and carnosine protected at the carboxyl group. The active derivative of hyaluronic acid is preferably an ester and is even more preferably the ester of 3-hydroxy-1,2,3,-benzotriazin-4(H)-one (HOOBT), whereas the carnosine dipeptide is preferably used in the form of methyl ester.

Other esters of carnosine or other active derivatives of hyaluronic acid, equivalent to the ester of HOOBT, can be used for this purpose.

The compound having formula (1) showed greater resistance to the action of human serum carnosinase with respect to the non-conjugated carnosine.

An object of the present invention also relates to pharmaceutical, cosmetic or nutraceutical compositions, comprising the compound having formula (1) as active principle. Considering the antioxidant, antiglycation, antiplatelet and chelating properties with respect to transition metals, the compositions containing the compound having formula (1) can be used for the treatment or prevention of conditions in which the formation of free radicals or the impaired conformation of proteins, due to both glycation and other causes, have a pathogenic role. Examples of these conditions comprise: cataract, dry eye, aging of the wounds, gastric lesions, diabetes, impaired immunomodulation response, diseases, liver diseases, tumoral and neurological pathologies (aging of the central nervous system, Alzheimer disease), damage due to ischemia/reperfusion.

An object of the present invention therefore relates to pharmaceutical, cosmetic or nutraceutical compositions, comprising the compound having formula (1) as active principle, for use in the treatment and/or prevention of protein conformational disorders and conditions such as cataract, dry eye, aging of the skin, wounds, gastric lesions, diabetes, impaired immunomodulation response, kidney diseases, liver diseases, tumoral and neurological diseases, damage due to ischemia/reperfusion. These compositions, in fact, have a cicatrizing, gastroprotective, preferably as a complex with $Zn^{2+}$, glucomodulatory, immunomodulatory, antitumor, antigenotoxic, neuroprotective activity, anti-aging of the central nervous system, protective activity for damage due to ischemia/reperfusion, nephroprotective and hepato-protective activity.

Doses and administration routes depend on the conditions which are generally determined by clinical experts, usually ranging, however, from 100 to 5000 mg/die per os, and from 0.1 to 10% by weight for formulations for topic or systemic use (i.e. infective).

Possible examples of formulations comprise: capsules, tablets, granules, powders, solutions, ointments, gels, eye-drops and any other formulation known to the expert of formulation.

Possible administration routes are obviously related to the disease to be treated, and, for illustrative purposes, may include oral, topical, local-regional, intramuscular, intradermal, intraocular, intra- or peri-articular, infusive, etc.

An example which illustrates the invention is provided hereunder.

Unless otherwise indicated, commercially available reagents were used, treated as follows, when necessary: anhydrous methanol (SIGMA, MeOH), used for the synthesis of carnosine methyl-ester, was kept for 24 hours on 4 Å molecular sieves before being used.

The carnosine methyl-ester (Car-OMe) was synthesized, treating the carnosine (Sigma) with hydrochloric acid in methanol at 0° C. Acetyl chloride was used as HCl source.

The ¹H-NMR spectra were registered on a Varian instrument at 500 MHz (Inova 500), using HOD frequency as reference.

Experiments aimed at determining the molecular weight distribution (MWD) and the intrinsic viscosity of the conjugated HyCar were effected on a CPG/SEC chromatographic system equipped with a Malvern triple detector (ViscoteckTDmax).

The fluorescence measurements were effected on a SHIMADZU RF-5301 PC spectrofluorophotometer, whereas the UV-vis absorption measurements were effected on a SHIMADZU UV-1800 or Beckman DU 650 spectrophotometer.

The SOD-like activity of the Cu(II) complex of conjugated HyCar and those of the Cu(II) complex of carnosine or HA, were determined by means of the Fridovich test (*Anal. Biochem.* 44, 276, 1971).

In order to prepare said Cu(II) complexes, cupric nitrate was used in aqueous solution at the following concentrations: $[L]=[Cu(II)]=10^{-6}\_10^{-7}$; it is in fact known to the skilled in the art that carnosine easily forms chelates with transition metals (Free Red Res. Commun.; 1991, 12-13 pt. 1, 179-185). All the chemical products used were purchased from Sigma.

The HPLC analysis of the oligosaccharides produced following the enzymatic digestion of HyCar or free hyaluronic acid with bovine testicular hyaluronidase, was carried out on an Agilent 1200 chromatographic system with a UV detector, using a Supelcosil LC-SAX1 column (25×4.6 cm; Supelco) and reading the chromatographic profile at a wavelength of 214 nm. Elution: flow 1.2 ml/min; isocratic NaCl 50 mM (pH 4) for 5 min, then, programmed to NaCl 1.2 M (pH 4) in 60 min.

EXAMPLE

Synthesis of conjugated 3-N-hyaluronyl of 2-(3-aminopropanamide)-3-(1H-imidazol-4-yl)propanoic acid (HyCar)

In a typical synthesis procedure, one gram of sodium hyaluronate (195 KDa) was added, under stirring, to 20 ml of cold tetrahydrofuran (THF) at 5° C. The following products were added in sequence to the resulting suspension: 20 ml of a solution of $H_2O$/THF (1:1 v/v) containing 0.5 mmoles of HOOBT, 10 ml of a solution of $H_2O$/THF (1:1 v/v) containing 0.2 mmoles of tris[2-(2-methoxyethoxy)ethyl]amine, and 5 ml of a methanol solution containing 0.125 mmoles of L-canosine methylester. After 30 minutes at 5° C., 10 ml of a solution of N-(3-Dimethylaminopropyl)-N'-ethyl-carbodiimide hydrochloride (EDC.HCl; 0.25 mmoles) were added to the mixture and the whole reaction mass was left under continuous stirring at 5° C. for 20 hours. After this period, the reaction mixture was treated with 100 ml of a solution of NaOH 0.1N and left to rest at 5° C. for a further 3.5 hours. At this point, the pH of the mixture was brought to 7.0 with 2N HCl, and the conjugate was precipitated by the addition of 800 ml of acetone. The product of interest was then removed from the supernatant by centrifugation and subsequently dialyzed against water for 60 hours. The conjugate was then recovered and lyophilized (yield 70%).

¹H NMR ($D_2O$, 500 MHz) (ppm): 8.66 (singlet; H-2 of the imidazole ring), 7.34 (singlet; H-5 of the imidazole ring), 4.61-4.52 (broad multiplet; H-6 of the residues of glucuronic acid, H-1 of the residues of N-acetylglucosamine and H-2 of the chain of propanoic acid), 3.90-3.23 (broad multiplet; H-2, H-3, H-4 and H-5 of the residues of glucuronic acid, H-2, H-3, H-4, H-5, 2H-6 of the residues of N-acetyl glucosamine and C-3 methylene of the propanamide group), 3.17 (multiplet; 2H-3 of the chain of propanoic acid, 2.44 (multiplet; methylene C-2 of the propanamide group), 2.06 (broad singlet $CH_3$ of the residues of N-acetylglucosamine). The ¹H NMR spectrum of the conjugated HyCar with the main assignments is indicated in FIG. 1 which shows the resonances used for calculating the percentage of carboxyl groups linked with an amide bridge to carnosine units (loading %).

The quantity of carnosine present in the conjugate is determined from the ratio between the integration value of the signal at 2.06 ppm (relating to the acetyl groups of HA) and the integration value of the signal at 2.44 ppm (relating to C-3 of the propanamide group), or one of the H-2 or H-5 signals of the imidazole ring (at 8.66 and 7.34 ppm, respectively).

Following the synthesis procedure described above, the percentage of carboxyl groups present in the polysaccharide unit of the conjugate that formed the amide bond with carnosine proved to be equal to 7%. By suitably modifying the stoichiometric ratios between HA and the other reagents, conjugation values of up to 25% were obtained.

Intrinsic Viscosity and Molecular Weight Distribution of the Conjugate HyCar

The parameters indicated above were determined by means of size exclusion chromatography carried out on the chromatographic system GPCmax VE 2001 (Malvern), equipped with two TSK-GEL GMPWXL columns (7.8 mm ID×30 cm; Viscotek-TOSOH BIOSCIENCE) installed in series. The system is coupled with a system of three detectors positioned in series and comprising: a refraction index detector, a light scattering detector and a four-capillary differential viscometer. The sample was eluted using an aqueous solution 0.1M of sodium nitrate containing 0.5 g/L of sodium azide with a flow of 0.6 ml/min, at 40° C. The software Omnisec 4.1 was used for the acquisition and data analysis.

Figure 2:
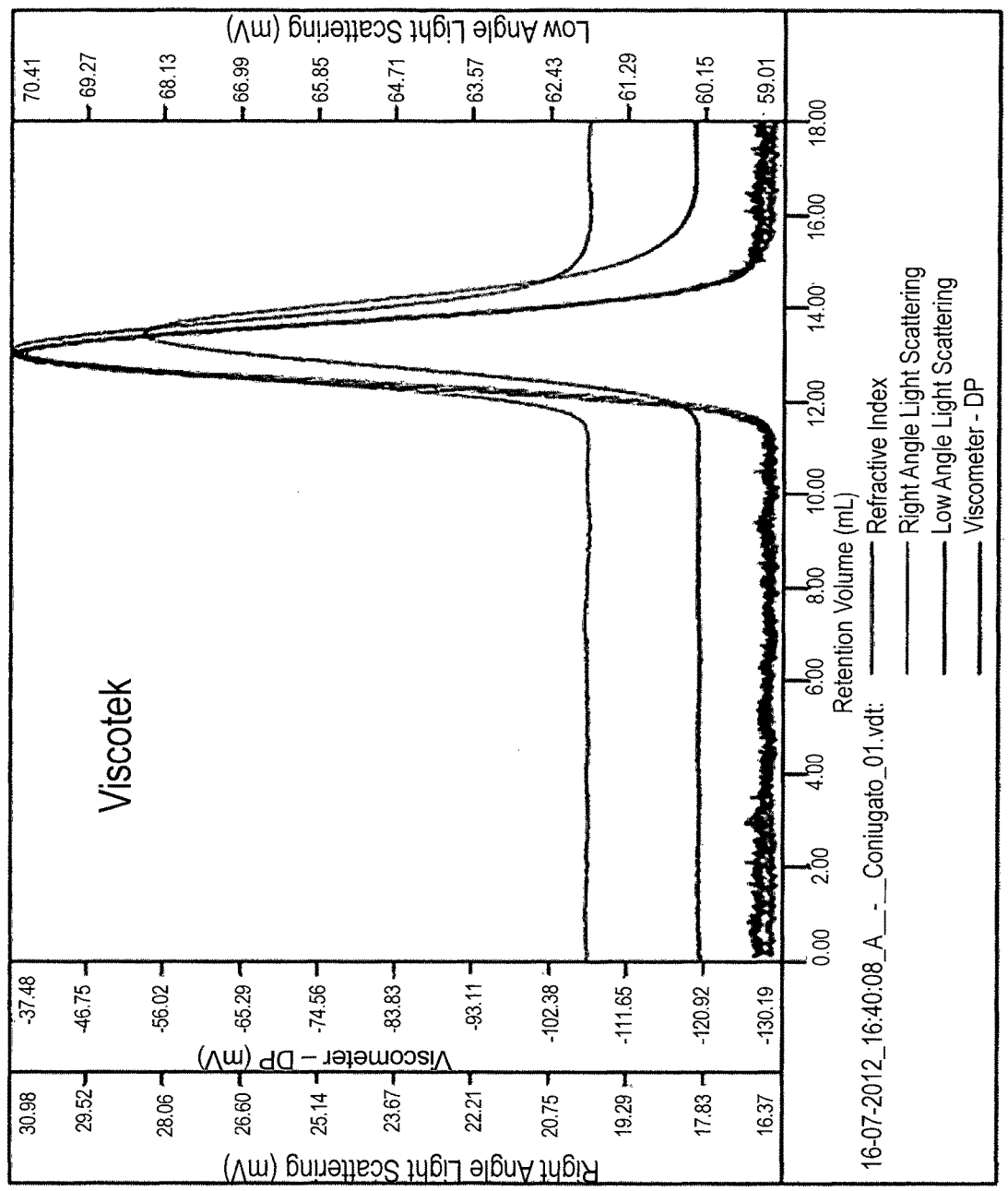

FIG. 2 shows a typical chromatogram obtained for HyCar (loading 7%) which indicates the chromatographic behaviour of a sample of HyCar (7% loading) on a TSK-GEL GMPWXL column. The triple-detector detection was effected on Viscotek TDA 302 (Malvern).

The physical parameters relating to the intrinsic viscosity and molecular weight (MW), determined at different concentrations for the conjugate of hyaluronic acid-carnosine, compared with those of the corresponding hyaluronic acid, determined by means of size exclusion chromatography coupled with a triple detector, are indicated in Table 1 below.

TABLE 1

| Sample | Theoretical Conc. (mg/ml) | Conc. found (mg/ml) | Molecular weight (MW) | Intrinsic viscosity (dl/g) |
| --- | --- | --- | --- | --- |
| HA 190 kD (D) | 0.5 mg/ml | 0.513 | 190713 | 5.2 |
| HA 190 kD (E) | 0.25 mg/ml | 0.261 | 192830 | 5.2 |
| HA 190 kD (F) | 0.1 mg/ml | 0.109 | 194713 | 5.3 |
| HyCar (7%)190 kD | 0.5 mg/ml | 0.420 | 196758 | 4.8 |
| HyCar (7%)190 kD | 0.25 mg/ml | 0.205 | 200258 | 4.8 |
| HyCar (7%)190 kD | 0.1 mg/ml | 0.081 | 204370 | 4.9 |

Figure 3:
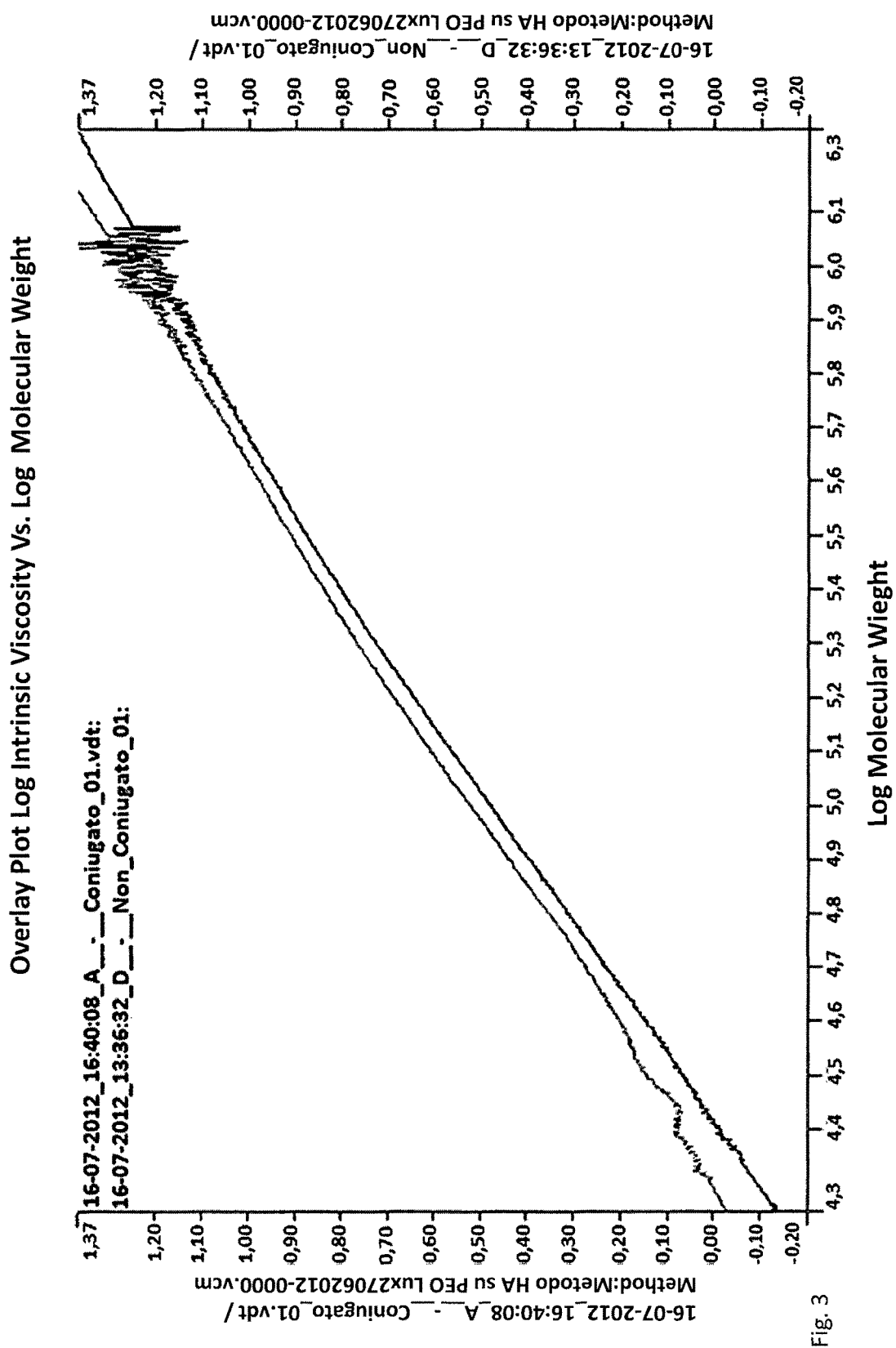

FIG. 3 shows, as an example, the Mark-Howink graph (viscosity log towards the molecular weight log, MW) of the conjugate of hyaluronic acid-carnosine (loading 7%) compared with that of non-conjugated hyaluronic acid: more specifically, the graph was obtained for a solution (0.5 mg/ml) of HyCar (7% loading) compared with a solution, at the same concentration, of the corresponding non-conjugated hyaluronic acid.

The results showed that the intrinsic viscosity of the HyCar conjugate is only slightly lower than that of the non-conjugated hyaluronic acid having the same MW, whereas the weight average molecular weight of the conjugate is coherently greater than that of the parent polysaccharide. This means that the conjugation does not alter the physico-chemical characteristics of HA, from which its rheological behavior depends on. This is very important especially in the phase of formulating the product, when it is necessary to establish a priori the rheological parameters of the finished product (viscosity, smoothness, etc.).

SOD-like Antioxidant Activity

The SOD-like activity of the Cu(II) complex of the HyCar conjugate was determined using the indirect method of Fridovich (*Anal. Biochem.* 44, 276, 1971). The superoxide anion was enzymatically generated by the xanthine-xanthine oxidase System and spectrophotometrically followed by monitoring the reduction of nitro blue tetrazolium (NBT) at 560 nm. The reaction mixture contained: cytochrome c (30 µM) or NBT (250 µM), xanthine (50 µM), in a phosphate buffer (10 mM) at pH 7.4. An appropriate quantity of xanthine-oxidase was added to 2 ml of this mixture so as to produce a $\Delta A$ $min^{-1}$ of 0.024. This corresponds to a production rate of $O_2^{\cdot-}$ equal to 1.1 µM $min^{-1}$. The reduction rate of the chromogenic molecule was measured in the presence and in the absence of the complex under examination for 600 seconds. All the measurements were effected at 25±0.2° C. using cuvettes having an optical path of 1 cm, thermostat-regulated and equipped with magnetic stirring. In order to exclude possible inhibition of the xanthine-oxidase activity, the production of uric acid on the part of xanthine oxidase was spectrophotometrically followed at 295 nm, in separate experiments.

Figure 4:
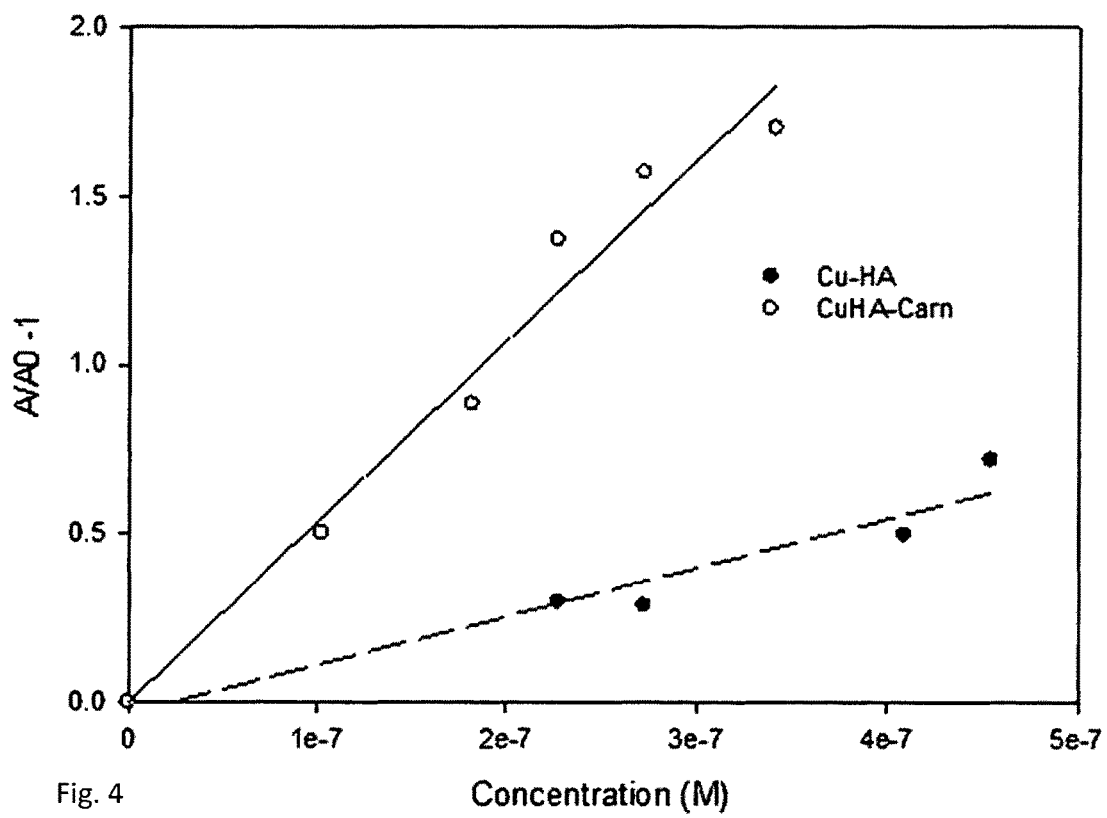

The $I_{50}$ values (i.e the concentration that produces a 50% inhibition of the reduction of NBT) of the metal complexes under examination, determined at pH 7.4, are indicated in FIG. 4 and in Table 2 below.

TABLE 2

| Complex | $I_{50}$ µM |
|---|---|
| SOD | 0.014 (±0.003) |
| Cu/HyCar (7%) | 0.21 (±0.04) |
| Cu/Car | 0.8 (±0.16) |
| Cu/HA | 1.0 (±0.2) |

Table 2 therefore indicates the SOD-like activities of the Cu(II) complexes of HyCar, Car and HÁ, expressed as concentrations capable of inhibiting 50% of the reduction of NBT ($I_{50}$).

More specifically, FIG. 4 indicates the SOD-like activities of the Cu(II) complexes of (Cu-HyCar) and non-conjugated HA (Cu-HA), determined by means of the indirect method proposed by Fridovich according to the operative specifications described above. Clearly, the smaller is the quantity of product used to obtain the value of I50, the greater is its antioxidant activity. From the analysis of the data, it appears evident that the conjugate Cu/Hycar has an antioxidant activity about 4 times higher than that of Cu/Car. Given that the complex Cu/HA, as expected, has a very low antioxidant activity, the result obtained with Cu/Hycar is surprising and unexpected, and it demonstrates the synergy due to the particular type of conjugation HA/Carnosine through the amide bond, as here described.

Enzymatic Hydrolysis on the Part of Human Serum Carnosinase

The time-dependent stability of HyCar with respect to human serum carnosinase, compared with the stability of the mixture of carnosine+HA or carnosine alone, was determined by incubating each of these substances (900 µM) at 37° C. in 50 mM Tris/HCl (pH 8.0) with the above-mentioned enzyme (CN1), purified by the culture medium of Hela cells stably transfected as previously indicated (Antioxid. Redox Signal., 11, 2759, 2009). A parallel experiment was effected as negative control, in which hyaluronic acid alone was subjected to enzymatic action. The course of the reaction was followed by collecting, at various time intervals, 50 µl aliquots of the mixture for a total of 5 hours, and, after deproteinization with trichloroacetic acid (TCA), fluorometrically determining the quantity of histidine in the final solution, after reaction with ortho-phthalic aldehyde (OPA; Fluka), according to a procedure already described (Clin. Chim. Acta, 1982, 123, 221). The results are indicated in FIG. 5.

Figure 5:
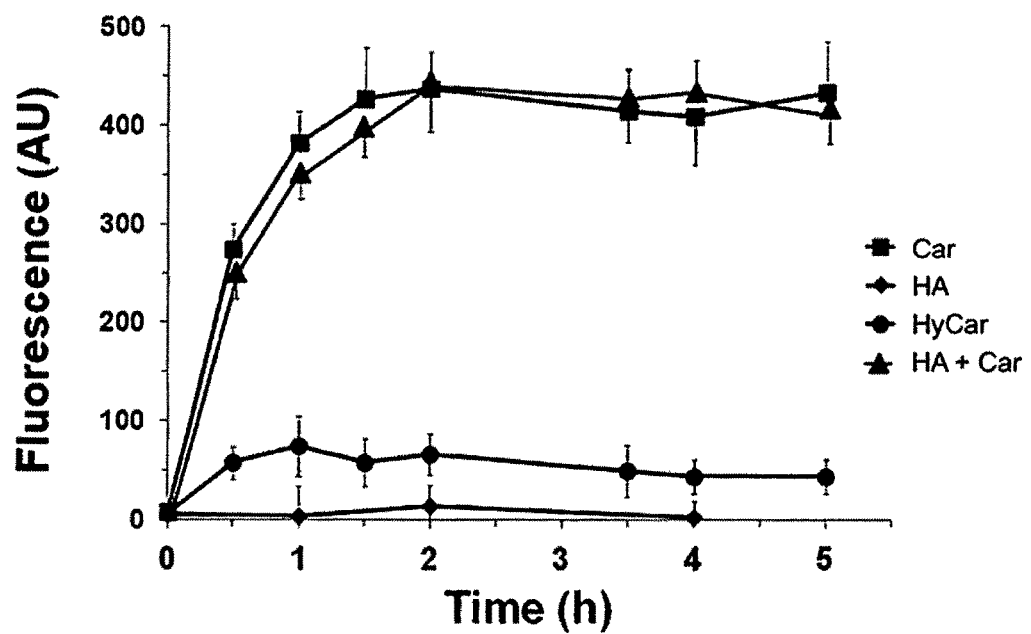

More specifically, FIG. 5 indicates the stability with time of HyCar (●), subjected to the action of human serum carnosinase, compared with the stability of carnosine (■), carnosine+HA (▲), and HA alone (♦)(the latter used as negative control of the experiment). The histidine released was spectrophotometrically determined as OPA-derivative.

Enzymatic Hydrolysis on the Part of Bovine Testicular Hyaluronidase

The stability of the HyCar conjugate with respect to Hyaluronidase (bovine testicular Hyaluronidase, Sigma) was evaluated by incubating the same (250 µL, 20 mg/mL) for 2 h at 37° C. in a buffer (Sodium Acetate 100 mM, NaCl 150 mM, pH 5.2) with 1,500 units of enzyme. After this period of time, the hydrolyzate was analyzed in HPLC on an anion-exchange column under the experimental conditions described under item [0024] and previously cited in literature (Anal. Chem., 2007, 6390-6397). In a parallel experiment, free hyaluronic acid was used as substrate for the same enzyme under the same experimental conditions. In both cases, a similar chromatographic profile was obtained, characterized by the presence of degradation products essentially consisting of tetrameric and hexameric glycide units.

BIBLIOGRAPHICAL REFERENCES CITED IN THE DESCRIPTION

The following list indicates the bibliographical references mentioned by the Applicant, produced solely for the convenience of the reader. The same should not be considered as being part of the patent document. Even if prepared with the utmost care, possible errors or omissions cannot be excluded. No responsibility is therefore assumed in this respect.

Patents cited in the description:
U.S. Pat. No. 4,508,728 A;
DE 4316293;
WO 0152808 A;
WO 9510294 A;
EP 1176154 A;
EP 1860116 A1;
WO 2012/076961 A2;

Non-patent literature mentioned in the description:
Biochim. Biophys. Acta, 2002, vol. 1570, 89;
Molecules and Cells, 2002, vol. 13, 498;
Biochem. J., 1988, vol. 967, 241;
Biochem. Int., 1987, vol. 15, 1105;
Biochim. Biophys. Acta, 1989, vol. 1004, 363;

Eur. J. Med. Chem., 2008, vol. 43, 373;
Helv. Chim. Acta, 2002, vol. 85, 1633;
J. Neurosci. Res. 2007, vol. 85, 2239;
Neurochem. Res., 2010, vol. 35, 2144;
Mol. Aspects Med., 2011, vol. 32, 258;
Neurochem. Res., 2013, vol. 38, 50;
Dalton Trans., 2003, 4406;
Biomed. Res. Trace Elem., 2001, vol. 12, 159;
Clinical Chim. Acta, 1996, vol. 254, 1;
J. Am. Chem. Soc., 1998, vol. 120, 7030;
Biomedical applications of hyaluronic acid. ACS Publications, 2006, p. 155-74;
Biomaterials, 2004, vol. 25, 1339;
Calcified Tissue Int., 1971, vol. 7, 175;
Dumitriu S., Polymeric biomaterials. New York: Marcel Dekker, 2002. ISBN: 0-8247-8969-5;
Garg H. G., Hales C. A., Chemistry and biology of hyaluronan. Oxford: Elsevier Science, 2004. ISBN: 978-0-08-044382-9;
Biomaterials, 2005, vol. 26, 359;
Nat. Rev. Cancer, 2004, vol. 4, 528;
J. Surg. Res., 2008, vol. 147, 247;
J. Cell Sci., 1992, vol. 103, 293;
Vet. Med., 2008, vol. 53, 397;
Acta Biomater., 2010, vol. 6, 2407;
Biomaterials, 2007, vol. 28, 1830;
J. Control. Release, 2000, vol. 69, 169;
Chem. Rev., 2001, vol. 101, 1869;
Biomaterials, 2003, vol. 24, 4337;
Int. J. Tissue React., 2002, vol. 24, 65;
Acta Biomater., 2013, vol. 9, 7081;
Anal. Biochem., 1971, vol. 44, 276;
Clin. Chim. Acta, 1982, vol. 123, 221;
Anal. Chem., 2007, 6390-6397;
Free Red Res. Commun., 1991, 12-13 pt. 1, 179-185.

The invention claimed is:
1. A compound having formula (1)

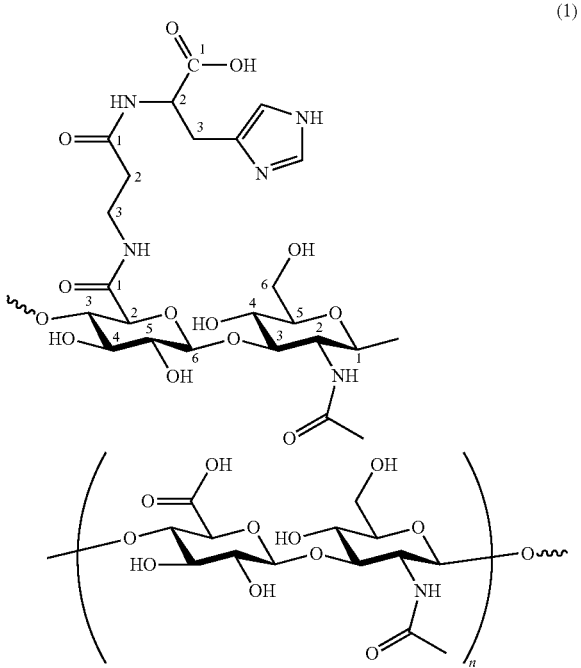

(1)

2. The compound according to claim 1, wherein the percentage of the carboxylic groups of hyaluronic acid conjugated by the formation of an amide bond with carnosine ranges from 2 to 25%, preferably from 5 to 20%, and is preferably equal to 7%.

3. The compound according to claim 1, wherein the hyaluronic acid has a weight average molecular weight ranging between 90 and 230 kDa, preferably between 180 and 210 kDa.

4. The compound according to claim 1, wherein the hyaluronic acid has a weight average molecular weight ranging between 500 and 730 kDa.

5. The compound according to claim 1, wherein compound having formula (1) is in the form of a complex of Cu(II).

6. A process for the preparation of the compound according to claim 1, wherein an active derivative of hyaluronic acid is covalently conjugated with a carnosine, preferably protected at the carboxyl group.

7. The process according to claim 6, wherein the active derivative of hyaluronic acid is an ester, and is preferably the ester of 3-hydroxy-1,2,3,-benzotriazin-4(H)-one.

8. The process according to claim 6, wherein the carnosine is protected at the carboxyl group by the formation of a methyl ester.

9. Pharmaceutical, cosmetic or nutraceutical compositions, comprising, as active principle, the compound having formula (1) according to claim 1.

conjugate of carnosine dipeptide having formula (2)

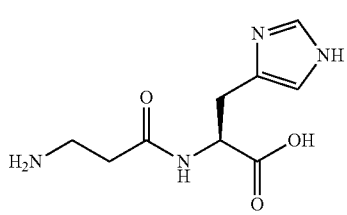

(2)

with hyaluronic acid, wherein the conjugation is effected by the formation of an amide bond between the $NH_2$ group of carnosine, preferably protected at the carboxyl group, and one or more carboxylic groups of hyaluronic acid, preferably of an active derivative of hyaluronic acid, even more preferably a COX ester having formula (3)

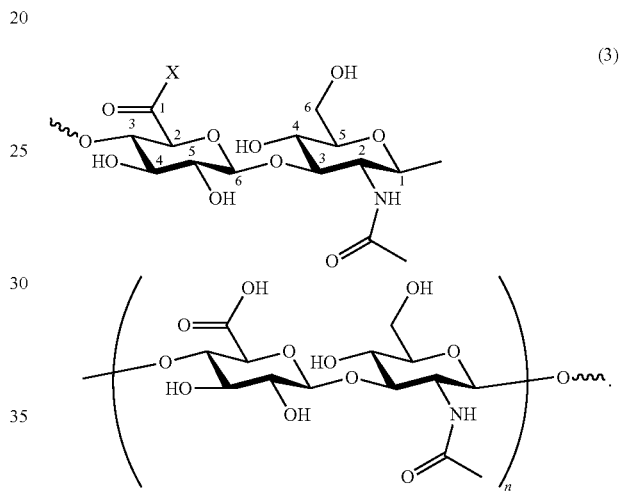

(3)

10. Pharmaceutical, cosmetic or nutraceutical compositions comprising, as active principle, the compound having formula (1) according to claim 1, for use in the treatment and/or prevention of protein conformational disorders and conditions such as cataract, dry eye, skin aging, wounds, gastric lesions, diabetes, impaired immune response, kidney diseases, liver diseases, tumoral and neurological diseases, damage due to ischemia/reperfusion.

11. The compound according to claim 2, wherein the hyaluronic acid has a weight average molecular weight ranging between 90 and 230 kDa, preferably between 180 and 210 kDa.

12. The compound according to claim 2, wherein the hyaluronic acid has a weight average molecular weight ranging between 500 and 730 kDa.

13. A process for the preparation of the compound according to claim 2, wherein an active derivative of hyaluronic acid is covalently conjugated with a carnosine, preferably protected at the carboxyl group.

14. A process for the preparation of the compound according to claim 3, wherein an active derivative of hyaluronic acid is covalently conjugated with a carnosine, preferably protected at the carboxyl group.

15. A process for the preparation of the compound according to claim 4, wherein an active derivative of hyaluronic acid is covalently conjugated with a carnosine, preferably protected at the carboxyl group.

16. A process for the preparation of the compound according to claim 5, wherein an active derivative of hyaluronic acid is covalently conjugated with a carnosine, preferably protected at the carboxyl group.

17. The process according to claim 7, wherein the carnosine is protected at the carboxyl group by the formation of a methyl ester.

* * * * *